(12) United States Patent
Xu et al.

(10) Patent No.: US 10,321,682 B2
(45) Date of Patent: Jun. 18, 2019

(54) PESTICIDAL ARYL PYRROLE NITRILE COMPOUND, PREPARATION METHOD FOR SAME, USES THEREOF, AGRICULTURAL PESTICIDE, AND PEST CONTROL METHOD

(71) Applicant: HENAN GOODDAYS BIOLOGY DEVELOPMENT CO., LTD., Jinshui District Zhengzhou, Henan (CN)

(72) Inventors: Bo Xu, Henan (CN); Xuejie Liang, Henan (CN); Changhong Li, Henan (CN); Gangchao Ran, Henan (CN); Yanli Ding, Henan (CN)

(73) Assignee: HENAN GOODDAYS BIOLOGY DEVELOPMENT CO., LTD., Jinshui District (CN)

( * ) Notice: Subject to any disclaimer, the term of this patent is extended or adjusted under 35 U.S.C. 154(b) by 0 days.

(21) Appl. No.: 16/080,008

(22) PCT Filed: Jan. 23, 2017

(86) PCT No.: PCT/CN2017/000131
§ 371 (c)(1),
(2) Date: Aug. 26, 2018

(87) PCT Pub. No.: WO2017/143872
PCT Pub. Date: Aug. 31, 2017

(65) Prior Publication Data
US 2019/0059379 A1 Feb. 28, 2019

(30) Foreign Application Priority Data
Feb. 26, 2016 (CN) .......................... 2016 1 0105846

(51) Int. Cl.
*A01N 43/78* (2006.01)
*A01N 25/04* (2006.01)
*A01N 25/14* (2006.01)
*A01N 25/12* (2006.01)
*A01N 25/30* (2006.01)
*C07D 417/06* (2006.01)

(52) U.S. Cl.
CPC ............ *A01N 43/78* (2013.01); *A01N 25/04* (2013.01); *A01N 25/12* (2013.01); *A01N 25/14* (2013.01); *C07D 417/06* (2013.01)

(58) Field of Classification Search
CPC ........ A01N 43/78; A01N 25/04; A01N 25/14; A01N 25/12; A01N 25/30; C07D 417/06
See application file for complete search history.

(56) References Cited

U.S. PATENT DOCUMENTS 5,187,184 A * 2/1993 Lovell .................... A01N 43/56
424/405

\* cited by examiner

*Primary Examiner* — John Pak
*Assistant Examiner* — Andriae M Holt
(74) *Attorney, Agent, or Firm* — Patshegen IP LLC; Moshe Pinchas

(57) ABSTRACT

The invention discloses an arylpyrrolecarbonitrile compound for insecticidal use, a preparation method and use thereof, an agricultural insecticide and a method for controlling pests. The preparation method comprises the following preparation steps: (1) 2-p-chlorophenyl-4-bromo-5-trifluoromethyl-3-cyanopyrrole, 2-chloro-5-chloromethylthiazole and potassium carbonate are provided as reaction starting materials in a ratio of the amount of substance of 1:1:1.2, and starting materials are put into a three-necked bottle together with DMF; (2) the materials are reacted at 60 to 100° C. for 1 to 4 hours; (3) the reaction is stopped after the completion of the reaction of the starting materials is detected, the materials are cooled to room temperature and filtered by suction to give 4-bromo-2-(4-chlorophenyl)-1-(2-chloro-5-thiazolylmethyl)-5-trifluoromethylpyrrole-3-carbonitrile as a white solid. The compound of the invention has a simple synthesis route, the needed starting materials are cheap and easy to obtain, the product has low production cost and has excellent broad-spectrum insecticidal activity against such plants as rice, cabbage and tomato.

13 Claims, No Drawings

PESTICIDAL ARYL PYRROLE NITRILE COMPOUND, PREPARATION METHOD FOR SAME, USES THEREOF, AGRICULTURAL PESTICIDE, AND PEST CONTROL METHOD

TECHNICAL FIELD

The invention relates to the field of agricultural insecticides, in particular to insecticidal arylpyrrolecarbonitrile compound, preparation method and use thereof, an agricultural insecticide and a method for controlling pests.

BACKGROUND

In the prior art, arylpyrrolecarbonitrile compounds have a very wide range of uses as agricultural insecticides. Chinese Patent ZL 88106516.1 discloses a series of arylpyrrole compounds developed by American Cyanamid Co., among which 4-bromo-2-(4-chlorophenyl)-5-trifluoromethylpyrrole-3-carbonitrile has an excellent biological activity of broad spectrum, but the phytotoxicity is relatively high. In order to reduce the phytotoxicity, American Cyanamid Co. found another compound, 4-bromo-2-(4-chlorophenyl)-1-ethoxymethyl-5-trifluoromethylpyrrole-3-carbonitrile (common name: chlorfenapyr, trade name: Chujin), through further optimization and screening. Chujin is high-efficient and broad-spectrum, has stomach toxicity, contact poisoning and systemic effects. It has moderate persistence on crops and excellent control effect on boring, sucking and chewing pests and mites. Chujin has a new mode of action, but its toxicity is relatively high. Its acute oral LD50 was 459 mg/kg for female rats, 223 mg/kg for male rats, and 0.5 mg/kg for Japanese carp.

SUMMARY OF THE INVENTION

An object of the present invention is to provide insecticidal arylpyrrolecarbonitrile compound with simple synthesis route, low cost and easy availability of raw materials, low production cost, excellent broad spectrum insecticidal activity, and preparation method and use thereof, as well as agricultural pesticides and method for controlling pests.

In order to achieve the above object, the present invention adopts the following technical solutions:

An insecticidal arylpyrrolecarbonitrile compound, as shown in formula (I):

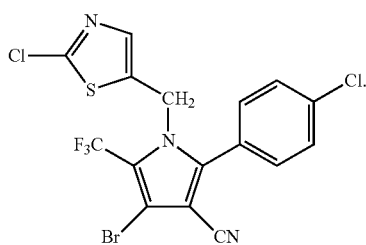

(I)

A method for preparing insecticidal arylpyrrolecarbonitrile compound, comprising the following preparation steps:
(1) 2-p-chlorophenyl-4-bromo-5-trifluoromethyl-3-cyanopyrrole, 2-chloro-5-chloromethylthiazole and potassium carbonate are provided as reaction starting materials in a ratio of the amount of substance of 1:1:1.2, and starting materials are put into a three-necked bottle together with DMF;
(2) the materials are reacted at 60 to 100° C. for 1 to 4 hours;
(3) the reaction is stopped after the completion of the reaction of the starting materials is detected, the materials are cooled to room temperature and filtered by suction to give 4-bromo-2-(4-chlorophenyl)-1-(2-chloro-5-thiazolylmethyl)-5-trifluoromethylpyrrole-3-carbonitrile as a white solid.

In step (1) of the above-mentioned method for preparing insecticidal arylpyrrolecarbonitrile compound, 35-105 g of 2-p-chlorophenyl-4-bromo-5-trifluoromethyl-3-cyanopyrrole, 17.8-51.4 g of 2-chloro-5-chloromethylthiazole, 17.85-53.55 g of potassium carbonate and 250-750 ml of DMF were added into a three-necked bottle.

In step (1) of the above-mentioned method for preparing insecticidal arylpyrrolecarbonitrile compound, 69.9 g of 2-p-chlorophenyl-4-bromo-5-trifluoromethyl-3-cyanopyrrole, 33.6 g of 2-chloro-5-chloromethylthiazole, 33.7 g of potassium carbonate and 500 ml of DMF were added into a three-necked bottle.

The use of the insecticidal arylpyrrolecarbonitrile compound is directed to the control of striped stem borer, rice leaf roller, beet armyworm, diamondback moth and cotton bollworm.

Agricultural insecticides prepared by using the above-mentioned insecticidal arylpyrrolecarbonitrile compound include the following dosage forms:
(1) suspension, the components of which consisting of 4-bromo-2-(4-chlorophenyl)-1-(2-chloro-5-thiazolylmethyl)-5-trifluoromethylpyrrole-3-carbonitrile, naphthalene sulfonate polycondensate, sodium dodecylbenzene sulfonate, xanthan gum, glycerol and water;
(2) granules, the components of which consisting of 4-bromo-2-(4-chlorophenyl)-1-(2-chloro-5-thiazolylmethyl)-5-trifluoromethylpyrrole-3-carbonitrile, sodium dodecylbenzene sulfonate, epoxy resin, pigment red and clay;
(3) wettable powder, the components of which consisting of 4-bromo-2-(4-chlorophenyl)-1-(2-chloro-5-thiazolylmethyl)-5-trifluoromethylpyrrole-3-carbonitrile, lignin carboxylate, sodium dodecylbenzenesulfonate and kaolin;
(4) water-dispersible granules, the components of which consisting of 4-bromo-2-(4-chlorophenyl)-1-(2-chloro-5-thiazolylmethyl)-5-trifluoromethylpyrrole-3-carbonitrile, naphthalene sulfonate polycondensate, sodium butylnaphthalene sulfonate, urea, kaolin, water and fructose(binder);
(5) microemulsion, the components of which consisting of 4-bromo-2-(4-chlorophenyl)-1-(2-chloro-5-thiazolylmethyl)-5-trifluoromethylpyrrole-3-carbonitrile, calcium dodecylbenzene sulfonate, styrene phenol polyoxyethylene ether, water and deionized water;
(6) aqueous emulsion, the components of which consisting of 4-bromo-2-(4-chlorophenyl)-1-(2-chloro-5-thiazolylmethyl)-5-trifluoromethylpyrrole-3-carbonitrile, xylene, alkylphenylpolyglycol ether, polyoxyethylene sorbitan ester, polyoxyethylene fatty acid ester, polyvinyl alcohol, isobutyl ester, propylene glycol and deionized water;
(7) emulsifiable concentrate, the components of which consisting of 4-bromo-2-(4-chlorophenyl)-1-(2-chloro-5-thiazolylmethyl)-5-trifluoromethylpyrrole-3-carbonitrile, xylene, sodium dodecylbenzenesulfonate and styrylphenol formaldehyde resin polyoxyethylene.

The agricultural insecticides prepared by using the above-mentioned insecticidal arylpyrrolecarbonitrile compound are prepared as follows:

(1) Preparation of suspension: 4-bromo-2-(4-chlorophenyl)-1-(2-chloro-5-thiazolylmethyl)-5-trifluoromethylpyrrole-3-carbonitrile, naphthalene sulfonate polycondensate, sodium dodecylbenzene sulfonate, xanthan gum, glycerin and water are mixed and pulped, firstly pre-dispersed with a high shear mixing emulsifier, and then the slurry is poured into a sand mill. Cooling water is introduced, the sand mill is turned on, sampling is taken at the discharge port, and the particle size is monitored with a particle size distribution meter. Once the median particle size $D_{50}$ reaches 2-3 microns, a suspension is obtained which contains 25 wt % of 4-bromo-2-(4-chlorophenyl)-1-(2-chloro-5-thiazolylmethyl)-5-trifluoromethylpyrrole-3-carbonitrile as active ingredient;

(2) Preparation of granules: 4-bromo-2-(4-chlorophenyl)-1-(2-chloro-5-thiazolylmethyl)-5-trifluoromethylpyrrole-3-carbonitrile, sodium dodecylbenzene sulfonate, epoxy resin, pigment red and clay are mixed and pulverized, and thereafter granulated using a disc granulator. After the granules are formed, they are dried by hot air, then cooled and sieved by passing respectively through 3 mm and 5 mm sieves. The particles passing through the 5 mm sieve and remaining on the mm sieve are the desired granules containing 2 wt % of 4-bromo-2-(4-chlorophenyl)-1-(2-chloro-5-thiazolylmethyl)-5-trifluoromethylpyrrole-3-carbonitrile as active ingredient;

(3) Preparation of wettable powder: 4-bromo-2-(4-chlorophenyl)-1-(2-chloro-5-thiazolylmethyl)-5-trifluoromethylpyrrole-3-carbonitrile, lignin carboxylate, sodium dodecylbenzene sulfonate and kaolin are mixed and pulverized, and thereafter pulverized by an ultrafine pulverizer, and the pulverized particle passing through a 325 mesh sieve is the desired wettable powder containing 10 wt % of 4-bromo-2-(4-chlorophenyl)-1-(2-chloro-5-thiazolylmethyl)-5-trifluoromethylpyrrole-3-carbonitrile as active ingredient;

(4) Preparation of water-dispersible granules: 4-bromo-2-(4-chlorophenyl)-1-(2-chloro-5-thiazolylmethyl)-5-trifluoromethylpyrrole-3-carbonitrile, naphthalene sulfonate polycondensate, sodium butyl naphthalene sulfonate, urea and kaolin are made into an ultrafine wettable powder, and then the wettable powder, water and fructose as binder are simultaneously introduced into a kneader to be kneaded to prepare a plastic material. Finally, the material was poured into an extrusion granulator for granulation with 3 mm pore size of the sieve, and dried and sieved to obtain a water-dispersible granule product containing 10 wt % of 4-bromo-2-(4-chlorophenyl)-1-(2-chloro-5-thiazolylmethyl)-5-trifluoromethylpyrrole-3-carbonitrile as active ingredient;

(5) Preparation of microemulsion: 4-bromo-2-(4-chlorophenyl)-1-(2-chloro-5-thiazolylmethyl)-5-trifluoromethylpyrrole-3-carbonitrile, calcium dodecylbenzene sulfonate, styrene phenol polyoxyethylene ether and water are thoroughly mixed into a uniform oil phase, and deionized water is slowly added under stirring, and then the reaction is heated under stirring, cooled to room temperature, and filtered to obtain a microemulsion product containing 20 wt % of 4-bromo-2-(4-chlorophenyl)-1-(2-chloro-5-thiazolylmethyl)-5-trifluoromethylpyrrole-3-carbonitrile as active ingredient;

(6) Preparation of an aqueous emulsion: 4-bromo-2-(4-chlorophenyl)-1-(2-chloro-5-thiazolylmethyl)-5-trifluoromethylpyrrole-3-carbonitrile, xylene, alkyl phenyl polyglycol ether, polyoxyethylene sorbitan ester, polyoxyethylene fatty acid ester, polyvinyl alcohol, isobutyl ester, propylene glycol and deionized water in prescribed ratio are added to a formulating kettle for mixing, and then homogeneous emulsification is carried out using a high shearing machine; the material is mixed under the condition of 2500 rpm for 1 hour to obtain a finished product with a suitable fineness and homogeneous mixing of various components, that is, an aqueous emulsion product containing 10 wt % of 4-bromo-2-(4-chlorophenyl)-1-(2-chloro-5-thiazolylmethyl)-5-trifluoromethylpyrrole-3-carbonitrile as active ingredient;

(7) Preparation of emulsifiable concentrate: 4-bromo-2-(4-chlorophenyl)-1-(2-chloro-5-thiazolylmethyl)-5-trifluoromethylpyrrole-3-carbonitrile, xylene, sodium dodecylbenzene sulfonate and styrylphenol formaldehyde resin polyoxyethylene are metered into a reaction vessel in prescribed ratio and mixed, and then left to stand to obtain an emulsifiable concentrate containing 10 wt % of 4-bromo-2-(4-chlorophenyl)-1-(2-chloro-5-thiazolylmethyl)-5-trifluoromethylpyrrole-3-carbonitrile as active ingredient.

A method for controlling pests by using an agricultural pesticide prepared by using the above-mentioned insecticidal arylpyrrolecarbonitrile compound comprises the following steps:
(1) determining the test field;
(2) partitioning and isolating the test field;
(3) identifying the test crops and target objects;
(4) determining the test conditions for application;
(5) determining the survey method after application.

The above method for controlling pests specifically includes the following steps:
(1) Determining the test field: the test field shall be flat, the irrigation shall be convenient, and the soil fertility shall be moderately superior;
(2) Partitioning and isolating the test field: all plots in the test field have the same cultivation and management conditions, using the same level of water and fertilizer management, and small ridges are built between the plots for isolation and protection. The plots are arranged in random groups; each plot is 20 square meters, and the trial is set to 5 replicates; each treatment is repeated 4 times;
(3) Identifying the test crops and target objects: ① the test crop is rice, the variety is Gangyou 725, the target objects are striped stem borer and rice leaf roller; ② the test crop is cabbage, the variety is Zhonggan 21, the target objects are diamondback moth and beet armyworm; ③ the test crop is tomato, the variety is Zhongza 9 and the target object is cotton bollworm;
(4) Determining the test conditions for application: ① when the test crop is rice, application is carried out once using manual knapsack sprayer, and no agricultural operations such as control of other rice pests is carried out during the test; ② when the test crop is cabbage, application is carried out once through ditch during planting, and no agricultural operations such as control of other cabbage pests is carried out during the test; ③ when the test crop is tomato, application is carried out once using manual knapsack sprayer, and no agricultural operations such as control of other tomato pests is carried out during the test;

(5) determining the survey method after application: ① when the test crop is rice: the survey is carried out 7 days and 14 days after application, respectively; the survey method for striped stem borer: sampling is done by parallel jump method, 100 clusters of rice plants per plot are surveyed for total number of plants and the number of withered sheaths; the survey method for rice leaf roller: for 5 points per plot and 5 clusters per point, the total number of leaves and the number of rolled leaves are surveyed, and the number of surviving larvae in the rolled rice leaf is also investigated; from the total number of plants and the number of withered sheaths surveyed in the treated area and the control area, the rate of withered sheaths, the control effect for striped stem borer and the average control effect are calculated; from the total number of leaves and the number of rolled leaves surveyed in the treated area and the control area, the rate of rolled leaves, the control effect for rice leaf roller and average control effect are calculated, significance of difference is determined by Duncan's new multiple range test "DMRT" method; ② when the test crop is cabbage: the survey is carried out 25 days and 35 days after application, respectively; the survey method for beet armyworm and diamondback moth: the survey method is carried out when pests occur obviously in the blank control, and the number of live larvae at different ages are counted for 20 plants of crops in each plot, the whole plant is surveyed and the number of live pests is recorded; significance of difference of the control effect is determined by Duncan's new multiple range test "DMRT" method; ③ when the test crop was tomato: the survey is carried out 7 days and 14 days after application, respectively; the survey method for cotton bollworm: random sampling of 5 fixed points per plot and 15 plants fixed at each point with cotton bollworm larvae totals to 75 plants; the number of larvae is recorded before and after the application; significance of difference of the control effect is determined by Duncan's new multiple range test "DMRT" method.

The beneficial effects of the present invention are as follows:
(1) The compound prepared by the present invention are formed by a substitution reaction of 4-bromo-2-(4-chlorophenyl)-5-trifluoromethylpyrrole-3-carbonitrile with 2-chloro-5-chloromethylthiazole. The compound exhibits high insecticidal activity and low toxicity; the synthesis route is simple, the required raw materials are cheap and easy to obtain, and the product has low production cost;
(2) The agricultural insecticides prepared by using the compound prepared by the invention as an active ingredient have good control effects on such rice pests as striped stem borer and rice leaf roller, and have no obvious adverse effects on rice and such beneficial organism as rice field natural enemy insects;
(3) The agricultural insecticides prepared by using the compound prepared by the invention as an active ingredient have good control effects on tomato cotton bollworm, and have no obvious adverse effects on tomato and natural enemy insects;
(4) The agricultural insecticide prepared by using the compound prepared by the invention as an active ingredient has great control effect on cabbage beet armyworm and diamondback moth, and has a long-lasting effect, and no beneficial organisms such as cabbage and natural enemies are found. Obvious adverse effects. The agricultural insecticides prepared by using the compound prepared by the invention as an active ingredient have good control effects on cabbage beet armyworm and diamondback moth, and have no obvious adverse effects on cabbage and such beneficial organism as natural enemy insects.

DETAILED DESCRIPTION OF THE INVENTION

Preparation Example 1

Synthesis of 4-bromo-2-(4-chlorophenyl)-1-(2-chloro-5-thiazolylmethyl)-5-trifluoro-methylpyrrole-3-carbonitrile (I)

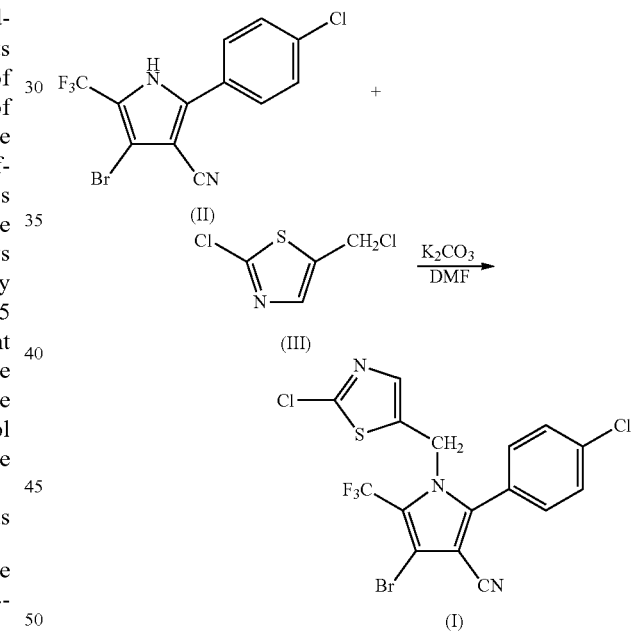

34.95 g (0.1 mol) of 2-p-chlorophenyl-4-bromo-5-trifluoromethyl-3-cyanopyrrole (II), 17.8 g (0.1 mol) of 2-chloro-5-chloromethylthiazole (III), 16.85 g (0.12 mol) of potassium carbonate and 250 ml of DMF were added into a 1 L three-necked flask, and reacted at 70° C. for 4 hours. The reaction was stopped when the completion of reaction of the starting materials was detected, cooled to room temperature, and filtered by suction to obtain 40.25 g (yield 83.67%) of white solid product. Mass spectrometry (electrospray ionization, positive ion mode) m/z 480 [M+H$^+$]. $^1$H-NMR (CDCl$_3$, 300 MHz, δ, ppm): 5.33 (s, 2H), 6.97 (s, 1H), 7.34 (d, J=8.3 Hz, 2H), 7.56 (d, J=8.3 Hz, 2H). $^{13}$C-NMR (CDCl$_3$, 75 MHz, δ, ppm): 43.4, 100.4, 103.7, 112.8, 119.2 (q, J=33.8 Hz), 120.0 (q, J=270.0 Hz), 124.8, 130.1, 131.0, 133.5, 137.8, 140.4, 143.5, 153.1.

Preparation Example 2

Synthesis of 4-bromo-2-(4-chlorophenyl)-1-(2-chloro-5-thiazolylmethyl)-5-trifluoro-methylpyrrole-3-carbonitrile (I)

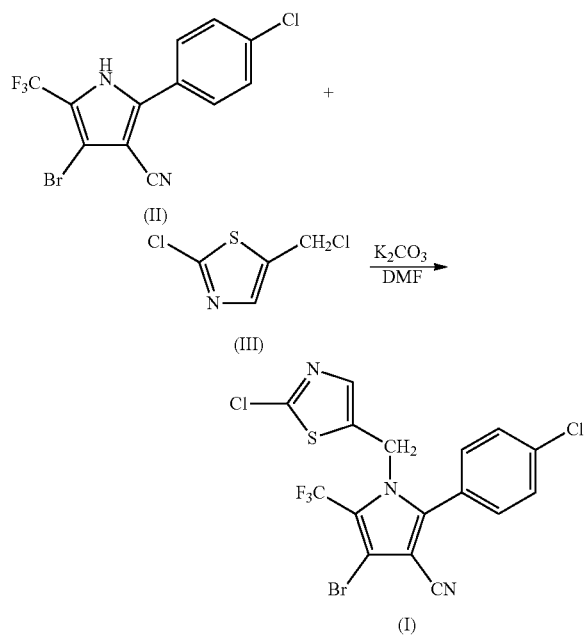

104.85 g (0.3 mol) of 2-p-chlorophenyl-4-bromo-5-trifluoromethyl-3-cyanopyrrole (II), 50.4 g (0.3 mol) of 2-chloro-5-chloromethylthiazole (III), 50.55 g (0.36 mol) of potassium carbonate and 800 ml of DMF were added into a 3 L three-necked flask, and reacted at 95° C. for 1.5 hours. The reaction was stopped when the completion of reaction of the starting materials was detected, cooled to room temperature, and filtered by suction to obtain 128.36 g (yield 88.93%) of white solid product. Mass spectrometry (electrospray ionization, positive ion mode) m/z 480 [M+H⁺]. $^1$H-NMR (CDCl$_3$, 300 MHz, δ, ppm): 5.33 (s, 2H), 6.97 (s, 1H), 7.34 (d, J=8.3 Hz, 2H), 7.56 (d, J=8.3 Hz, 2H). $^{13}$C-NMR (CDCl$_3$, 75 MHz, δ, ppm): 43.4, 100.4, 103.7, 112.8, 119.2 (q, J=33.8 Hz), 120.0 (q, J=270.0 Hz), 124.8, 130.1, 131.0, 133.5, 137.8, 140.4, 143.5, 153.1.

Preparation Example 3

Synthesis of 4-bromo-2-(4-chlorophenyl)-1-(2-chloro-5-thiazolylmethyl)-5-trifluoro-methylpyrrole-3-carbonitrile (I)

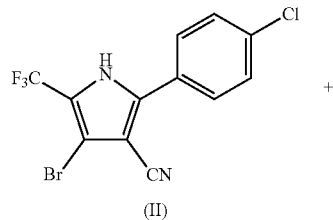

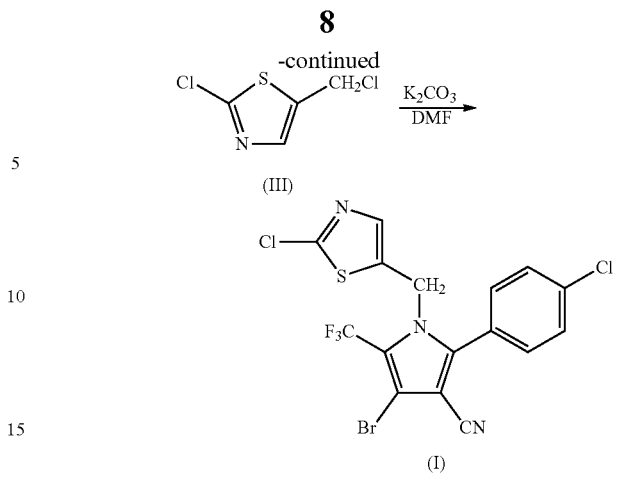

69.9 g (0.2 mol) of 2-p-chlorophenyl-4-bromo-5-trifluoromethyl-3-cyanopyrrole (II), 33.6 g (0.2 mol) of 2-chloro-5-chloromethylthiazole (III), 33.7 g (0.24 mol) of potassium carbonate and 500 ml of DMF were added into a 1 L three-necked flask, and reacted at 80° C. for 2 hours. The reaction was stopped when the completion of reaction of the starting materials was detected, cooled to room temperature, and filtered by suction to obtain 86.6 g (yield 90%) of white solid product. Mass spectrometry (electrospray ionization, positive ion mode) m/z 480 [M+H⁺]. $^1$H-NMR (CDCl$_3$, 300 MHz, δ, ppm): 5.33 (s, 2H), 6.97 (s, 1H), 7.34 (d, J=8.3 Hz, 2H), 7.56 (d, J=8.3 Hz, 2H). $^{13}$C-NMR (CDCl$_3$, 75 MHz, δ, ppm): 43.4, 100.4, 103.7, 112.8, 119.2 (q, J=33.8 Hz), 120.0 (q, J=270.0 Hz), 124.8, 130.1, 131.0, 133.5, 137.8, 140.4, 143.5, 153.1.

4-bromo-2-(4-chlorophenyl)-1-(2-chloro-5-thiazolylmethyl)-5-trifluoromethylpyrrole-3-carbonitrile prepared in Examples 1-3 has an acute oral LD$_{50}$ greater than 5000 mg/kg for both female rats and male rats. The acute percutaneous LD$_{50}$ for both female rats and male rats is greater than 2000 mg/kg, and the LC$_{50}$ for Japanese carp is 2.5 mg/kg. The toxicity was significantly lower than that of pesticides of the same type.

Preparation Example 4

Preparation of Suspension with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, naphthalene sulfonate polycondensate, sodium dodecylbenzene sulfonate, xanthan gum, glycerin and water are mixed and pulped, firstly pre-dispersed with a high shear mixing emulsifier, and then the slurry is poured into a sand mill. Cooling water is introduced, the sand mill is turned on, sampling is taken at the discharge port, and the particle size is monitored with a particle size distribution meter. Once the median particle size D$_{50}$ reaches 2-3 microns, a suspension is obtained which contains 25 wt % of 4-bromo-2-(4-chlorophenyl)-1-(2-chloro-5-thiazolylmethyl)-5-trifluoromethylpyrrole-3-carbonitrile as active ingredient.

Preparation Example 5

Preparation of Granules with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, sodium dodecylbenzene sulfonate, epoxy resin, pigment red and clay are mixed and pulverized, and thereafter granulated using a disc granulator. After the granules are formed, they are dried by hot air, then cooled and sieved by passing respectively through 3 mm and 5 mm sieves. The particles passing through the 5 mm sieve and remaining on the 3 mm sieve are the desired granules containing 2 wt % of 4-bromo-2-(4-chlorophenyl)-1-(2-chloro-5-thiazolylmethyl)-5-trifluoromethylpyrrole-3-carbonitrile as active ingredient.

Preparation Example 6

Preparation of Wettable Powder with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, lignin carboxylate, sodium dodecylbenzene sulfonate and kaolin are mixed and pulverized, and thereafter pulverized by an ultrafine pulverizer, and the pulverized particle passing through a 325 mesh sieve is the desired wettable powder containing 10 wt % of 4-bromo-2-(4-chlorophenyl)-1-(2-chloro-5-thiazolylmethyl)-5-trifluoromethylpyrrole-3-carbonitrile as active ingredient.

Preparation Example 7

Preparation of Water-Dispersible Granules Containing 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, naphthalene sulfonate polycondensate, sodium butyl naphthalene sulfonate, urea and kaolin are made into an ultrafine wettable powder, and then the wettable powder, water and fructose as binder are simultaneously introduced into a kneader to be kneaded to prepare a plastic material. Finally, the material was poured into an extrusion granulator for granulation with 3 mm pore size of the sieve, and dried and sieved to obtain a water-dispersible granule product containing 10 wt % of 4-bromo-2-(4-chlorophenyl)-1-(2-chloro-5-thiazolylmethyl)-5-trifluoromethylpyrrole-3-carbonitrile as active ingredient.

Preparation Example 8

Preparation of Microemulsion with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, calcium dodecylbenzene sulfonate, styrene phenol polyoxyethylene ether and water are thoroughly mixed into a uniform oil phase, and deionized water is slowly added under stirring, and then the reaction is heated under stirring, cooled to room temperature, and filtered to obtain a microemulsion product containing 20 wt % of 4-bromo-2-(4-chlorophenyl)-1-(2-chloro-5-thiazolylmethyl)-5-trifluoromethylpyrrole-3-carbonitrile as active ingredient.

Preparation Example 9

Preparation of Aqueous Emulsion with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, xylene, alkyl phenyl polyglycol ether, polyoxyethylene sorbitan ester, polyoxyethylene fatty acid ester, polyvinyl alcohol, isobutyl ester, propylene glycol and deionized water in prescribed ratio are added to a formulating kettle for mixing, and then homogeneous emulsification is carried out using a high shearing machine; the material is mixed under the condition of 2500 rpm for 1 hour to obtain a finished product with a suitable fineness and homogeneous mixing of various components, that is, an aqueous emulsion product containing 10 wt % of 4-bromo-2-(4-chlorophenyl)-1-(2-chloro-5-thiazolylmethyl)-5-trifluoromethylpyrrole-3-carbonitrile as active ingredient.

Preparation Example 10

Preparation of Emulsifiable Concentrate with 4-bromo-2-(4-chlorophenyl)-1-(2-chloro-5-thiazolylmethyl)-5-trifluoromethylpyrrole-3-carbonitrile as Active Ingredient 4-bromo-2-(4-chlorophenyl)-1-(2-chloro-5-thiazolylmethyl)-5-trifluoromethylpyrrole-3-carbonitrile, xylene as solvent, sodium dodecylbenzene sulfonate and styrylphenol formaldehyde resin polyoxyethylene are metered into a reaction vessel in prescribed ratio and mixed, and then left to stand to obtain an emulsifiable concentrate product containing 10 wt % of 4-bromo-2-(4-chlorophenyl)-1-(2-chloro-5-thiazolylmethyl)-5-trifluoromethyl-pyrrole-3-carbonitrile as active ingredient.

It shall be in particular noted that, in the preparation examples 4-10, 4-bromo-2-(4-chlorophenyl)-1-(2-chloro-5-thiazolylmethyl)-5-trifluoromethylpyrrole-3-carbonitrile is the active ingredient, and the rest are all auxiliary agents. It is a common knowledge in the art to add auxiliary agents for preparing the corresponding formulation. The amount of each auxiliary agent added is also prior art in the field, and those skilled in the art can select the amount added according to actual needs without any creative work.

Biological Working Examples

The following biological working examples 1 to 3 use the compound of the formula (1) 4-bromo-2-(4-chlorophenyl)-1-(2-chloro-5-thiazolylmethyl)-5-trifluoromethylpyrrole-3-carbonitrile as active ingredient to determine its biological activity.

Biological Working Example 1 Field Trial for Controlling Rice Pests

Referring to "GB/T 17980.1-2000 pesticides field efficacy test guidelines (1) insecticides for controlling borer pests from Lepidoptera", the formulation prepared in the preparation example 4 of the present invention was tested with respect to its field efficacy for controlling striped stem borer and rice leaf roller.

(1) Determining the Test Field:

The test was carried out in the test field of Luodian Village, Fudian Town, Huangchuan County, Xinyang City, Henan Province. The test field was flat, the irrigation was convenient, and the soil fertility was moderately superior;

(2) Partitioning and Isolating the Test Field:

All plots in the test field have the same cultivation and management conditions, using the same level of water and fertilizer management, and small ridges were built between the plots for isolation and protection. The plots were arranged in random groups; each plot was 20 square meters, and the trial was set to 5 replicates; each treatment was repeated 4 times;

(3) Identifying the Test Crops and Target Objects:

The test crop was rice, the variety was Gangyou 725, the target objects were striped stem borer and rice leaf roller;

(4) Determining the Test Conditions for Application:

The test time was August 2015, application was carried out once using manual knapsack sprayer, and no agricultural operations such as control of other rice pests was carried out during the test; it was cloudy on the day of the application, and there were no adverse weather conditions that affected the test results;

(5) Determining the Survey Method after Application:

The survey was carried out 7 days and 14 days after application, respectively, totaling two times; the survey method for striped stem borer: sampling was done by parallel jump method, 100 clusters of rice plants per plot were surveyed for total number of plants and the number of withered sheaths; the survey method for rice leaf roller: for 5 points per plot and 5 clusters per point, the total number of leaves and the number of rolled leaves were surveyed, and the number of surviving larvae in the rolled rice leaf was also investigated; from the total number of plants and the number of withered sheaths surveyed in the treated area and the control area, the rate of withered sheaths, the control effect for striped stem borer and the average control effect were calculated; from the total number of leaves and the number of rolled leaves surveyed in the treated area and the control area, the rate of rolled leaves, the control effect for rice leaf roller and average control effect were calculated, significance of difference was determined by Duncan's new multiple range test "DMRT" method; The test results are shown in Tables 1 and 2.

rate of withered sheaths (%)=number of withered sheaths/total number of plants surveyed×100 control effect for striped stem borer (%)=(rate of withered sheaths after application in control area−rate of withered sheaths after application in treated area)/rate of withered sheaths after application in control area×100 rate of rolled leaves (%)=number of rolled leaves/total number of leaves surveyed×100 control effect for rice leaf roller (%)=(rate of rolled leaves after application in control area−rate of rolled leaves after application in treated area)/rate of rolled leaves after application in control area×100

TABLE 1

Test results of field trial using the formulation prepared in preparation example 4 for controlling striped stem borer

| | | control effect | | | |
|---|---|---|---|---|---|
| | | 7 days after application | | 14 days after application | |
| formulations applied | dosage applied (amount of the formulations) | average control effect (%) | significance of difference* | average control effect (%) | significance of difference* |
| formulation prepared in the preparation example 4 | 4 g/mu | 74.39 | Bb | 71.23 | Bc |
| | 8 g/mu | 86.88 | Aa | 84.87 | Aab |
| | 12 g/mu | 88.29 | Aa | 87.36 | Aa |
| chlorantraniliprole suspension, 20 wt % | 10 g/mu | 85.08 | Aa | 82.09 | Ab |
| blank control | spray of clean water | / | | / | |

Note:
*uppercase letters indicate P = 0.01, lowercase letters P = 0.05. The 20 wt % chlorantraniliprole suspension differs from the preparation example 4 in that the active ingredients are different, but the preparation method and the amount of the added auxiliary agents are exactly the same.

TABLE 2

Test results of field trial using the formulation prepared in preparation example 4 for controlling rice leaf roller

| | | control effect | | | |
|---|---|---|---|---|---|
| | | 7 days after application | | 14 days after application | |
| formulations applied | dosage applied (amount of the formulations) | average control effect (%) | significance of difference* | average control effect (%) | significance of difference* |
| formulation prepared in the | 4 g/mu | 83.01 | Ab | 82.11 | Bb |
| | 8 g/mu | 89.57 | Aa | 90.30 | ABb |

TABLE 2-continued

Test results of field trial using the formulation prepared in preparation example 4 for controlling rice leaf roller

| formulations applied | dosage applied (amount of the formulations) | control effect | | | |
|---|---|---|---|---|---|
| | | 7 days after application | | 14 days after application | |
| | | average control effect (%) | significance of difference* | average control effect (%) | significance of difference* |
| preparation example 4 | 12 g/mu | 91.91 | Aa | 94.01 | Aa |
| chlorantraniliprole suspension, 20 wt % | 10 g/mu | 91.63 | Aa | 97.50 | Aa |
| blank control | spray of clean water | / | | / | |

Note:
*uppercase letters indicate P = 0.01, lowercase letters P = 0.05. The 20 wt % chlorantraniliprole suspension differs from the preparation example 4 in that the active ingredients are different, but the preparation method and the amount of the added auxiliary agents are exactly the same.

The test results showed that the formulation prepared in Preparation Example 4 had good control effect on striped stem borer and rice leaf roller, and the control effect was comparable to that of the control agent 20 wt % chlorantraniliprole suspension, and had no obvious adverse effects on rice and such beneficial organism as rice field natural enemy insects.

Biological Working Example 2 Field Trial for Controlling Cabbage Pests

Referring to "GB/T 17980.1-2000 pesticides field efficacy test guidelines (1) insecticides for controlling lepidoptera larvae of cruciferous vegetables", the formulation prepared in the preparation example 4 of the present invention was tested with respect to its field efficacy for controlling cabbage beet armyworm and diamondback moth.
(1) Determining the Test Field:
The test was carried out in the test field of Shilipu Village, Guandu Town, Zhongmu County, Zhengzhou City, Henan Province. The test field is flat, the irrigation is convenient, and the soil fertility is moderately superior;
(2) Partitioning and Isolating the Test Field:
All plots in the test field have the same cultivation and management conditions, using the same level of water and fertilizer management, and small ridges were built between the plots for isolation and protection. The plots were arranged in random groups; each plot was 20 square meters, and the trial was set to 5 replicates; each treatment was repeated 4 times;
(3) Identifying the Test Crops and Target Objects:
The test crop was cabbage, the variety is Zhonggan 21, and the target objects were diamondback moth and beet armyworm;
(4) Determining the Test Conditions for Application:
The test time was March 2015, application is carried out once using manual knapsack sprayer, and no agricultural operations such as control of other cabbage pests is carried out during the test; it was cloudy on the day of the application, and there were no adverse weather conditions that affected the test results;
(5) Determining the Survey Method after Application:
The survey was carried out 25 days and 35 days after application, respectively; the survey method for beet armyworm and diamondback moth: the survey method was carried out when pests occurred obviously in the blank control, and the number of live larvae at different ages were counted for 20 plants of crops in each plot, the whole plant was surveyed and the number of live pests was recorded; significance of difference of the control effect was determined by Duncan's new multiple range test "DMRT" method; the test results were shown in Tables 3 and 4.

effect of controlling pests (%)=(number of live pests in blank control area−number of live pests in treated area)/number of live pests in blank control area×100

TABLE 3

Test results of field trial using the formulation prepared in preparation example 4 for controlling diamondback moth

| formulations applied | dosage applied (amount of the formulations) | control effect | | | |
|---|---|---|---|---|---|
| | | 25 days after application | | 35 days after application | |
| | | average control effect (%) | significance of difference* | average control effect (%) | significance of difference* |
| formulation prepared in the preparation example 4 | 10 g/mu | 79.01 | bc | 77.96 | cd |
| | 15 g/mu | 84.83 | ab | 82.27 | bc |
| | 20 g/mu | 88.52 | a | 88.65 | a |
| chlorfenapyr suspension, 10 wt % | 50 g/mu | 77.55 | c | 76.28 | d |

TABLE 3-continued

Test results of field trial using the formulation prepared in preparation example 4 for controlling diamondback moth

| formulations applied | dosage applied (amount of the formulations) | control effect | | | |
|---|---|---|---|---|---|
| | | 25 days after application | | 35 days after application | |
| | | average control effect (%) | significance of difference* | average control effect (%) | significance of difference* |
| blank control | spray of clean water | / | | / | |

Note:
*lowercase letter P = 0.05; control effect of 10 wt % chlorfenapyr suspension is for 10 days after the application. The 10 wt % chlorfenapyr suspension differs from the preparation example 4 in that the active ingredients are different, but the preparation method and the amount of the added auxiliary agents are exactly the same.

TABLE 4

Test results of field trial using the formulation prepared in preparation example 4 for controlling beet armyworm

| formulations applied | dosage applied (amount of the formulations) | control effect | | | |
|---|---|---|---|---|---|
| | | 25 days after application | | 35 days after application | |
| | | average control effect (%) | significance of difference* | average control effect (%) | significance of difference* |
| formulation prepared in the preparation example 4 | 10 g/mu | 78.53 | Cc | 78.41 | Dd |
| | 15 g/mu | 83.54 | Bb | 87.50 | Bb |
| | 20 g/mu | 92.56 | Aa | 91.13 | Aa |
| chlorfenapyr suspension, 10 wt % | 50 g/mu | 84.78 | Bb | 82.69 | Cc |
| blank control | spray of clean water | / | | / | |

Note:
*uppercase letters indicate P = 0.01, lowercase letters P = 0.05; control effect of 10 wt % chlorfenapyr suspension is for 10 days after the application. The 10 wt % chlorfenapyr suspension differs from the preparation example 4 in that the active ingredients are different, but the preparation method and the amount of the added auxiliary agents are exactly the same.

The test results showed that the formulation prepared in Preparation Example 4 had good control effect against diamondback moth and beet armyworm, and the control effect was higher than that of the control agent 10 wt % chlorfenapyr suspension, and the effect was long lasting. No obvious adverse effects on cabbage and such beneficial organism as natural enemy insects was found.

Biological Working Example 3 Field Trial for Controlling Tomato Pests (1) Determining the Test Field:

The test was carried out in the trial field of Shilipu Village, Guandu Town, Zhongmu County, Zhengzhou City, Henan Province. The test field was flat, the irrigation was convenient, and the soil fertility was moderately superior;

(2) Partitioning and isolating the test field: all plots in the test field have the same cultivation and management conditions, using the same level of water and fertilizer management, and small ridges were built between the plots for isolation and protection. The plots were arranged in random groups; each plot was 20 square meters, and the trial was set to 5 replicates; each treatment was repeated 4 times;

(3) Identifying the Test Crops and Target Objects:

The test crop was tomato, the variety was Zhongza 9 and the target object was cotton bollworm;

(4) Determining the Test Conditions for Application:

The test time was May 2015, application was carried out once using manual knapsack sprayer, and no agricultural operations such as control of other tomato pests was carried out during the test; it was cloudy on the day of the application, and there were no adverse weather conditions that affected the test results;

(5) Determining the Survey Method after Application:

The survey was carried out 7 days and 14 days after application, respectively; the survey method for cotton bollworm: random sampling of 5 fixed points per plot and 15 plants fixed at each point with cotton bollworm larvae totaled to 75 plants; the number of larvae was recorded before and after the application; significance of difference of the control effect was determined by Duncan's new multiple range test "DMRT" method. The test results are shown in Table 5.

effect of controlling pests (%)=(number of live pests in blank control area−number of live pests in treated area)/number of live pests in blank control area×100

TABLE 5

Test results of field trial using the formulation prepared in preparation example 4 for controlling cotton bollworm

| | dosage applied | control effect | | | |
|---|---|---|---|---|---|
| | | 7 days after application | | 14 days after application | |
| formulations applied | (amount of the formulations) | average control effect (%) | significance of difference* | average control effect (%) | significance of difference* |
| formulation prepared in the preparation example 4 | 4 g/mu | 75.22 | b | 74.64 | c |
| | 8 g/mu | 83.88 | a | 83.23 | b |
| | 12 g/mu | 88.17 | a | 89.05 | a |
| Chlorantraniliprole/ lambda-cyhalothrin microcapsule suspension 14 wt % | 20 g/mu | 85.76 | a | 84.33 | b |
| blank control | spray of clean water | / | | / | |

Note:
*lowercase letters P = 0.05.

The test results showed that the formulation prepared in Preparation Example 4 had good control effect against tomato cotton bollworm, and the control effect was comparable to that of the control agent 14 wt % Chlorantraniliprole/lambda-cyhalothrin microcapsule suspension. No obvious adverse effects on cabbage and such beneficial organism as natural enemy insects was found.

It can be seen from the above examples that, the field trial results show that the compound of formula (I) of the present invention as an active ingredient has good control effect against rice stem borer, rice leaf roller and tomato bollworm. In the case of the same application amount per acre, the 25 wt % suspension obtained in the Preparation Example 4 has a good control effect against both striped stem borer and rice leaf roller, which is comparable to the control agent 20 wt % chlorantraniliprole suspension. The 25 wt % suspension obtained in Preparation Example 4 was applied in 4 g, 8 g and 12 g per mu, and the control effects 7 days after application against striped stem borer were 74%, 87% and 88%, respectively, and against rice leaf roller were 83%, 90% and 92%, respectively, without obvious adverse effects on rice and such beneficial organisms as rice field natural enemy insects. The 25 wt % suspension obtained in Preparation Example 4 was applied in 4 g, 8 g and 12 g per mu, and the control effects 7 days after application against tomato bollworm were 75%, 84% and 88%, respectively, which is comparable to the control agent 14 wt % Chlorantraniliprole/lambda-cyhalothrin microcapsule suspension, without obvious adverse effects on tomato and its natural enemy insects.

The compound of the formula (I) of the present invention as an active ingredient has good control effect against the cabbage beet armyworm and the diamondback moth. The 25 wt % suspension obtained in Preparation Example 4 was applied in 10 g, 15 g and 20 g per mu, and the control effects 35 days after application against beet armyworm were 78%, 87% and 91%, respectively, and against diamondback moth were 78%, 82% and 89%, respectively. That is higher than the control effect of 10 wt % control agent chlorfenapyr suspension applied by spray, and is long-lasting. There is no obvious adverse effect on cabbage and such beneficial organisms as natural enemy insects.

It is apparent that the above-described embodiments of the present invention are merely illustrative of the present invention and are not intended to limit the embodiments of the present invention. Other variations or changes may be made by those skilled in the art based on the above description, which cannot be exhaustively enumerated here. Obvious changes or variations which are derived from the technical solutions of the present invention are still within the scope of the present invention.

The invention claimed is:

1. An arylpyrrolecarbonitrile compound for insecticidal use, characterized in that it is as shown in formula (I):

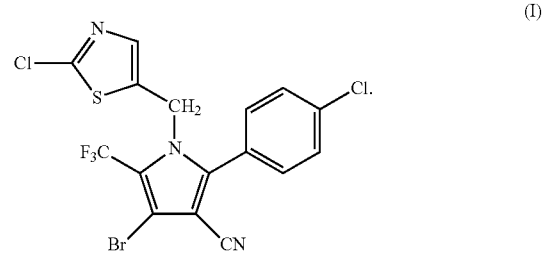 [SMILES: N#Cc1c(Br)c(C(F)(F)F)n(Cc2cnc(Cl)s2)c1-c1ccc(Cl)cc1]

2. Agricultural insecticide dosage forms prepared using the arylpyrrolecarbonitrile compound as claimed in claim 1, characterized in that the dosage forms are selected from the group consisting of:
   (1) suspensions, wherein the components consist of 4-bromo-2-(4-chlorophenyl)-1-(2-chloro-5-thiazolylmethyl)-5-trifluoromethylpyrrole-3-carbonitrile, naphthalene sulfonate polycondensate, sodium dodecylbenzene sulfonate, xanthan gum, glycerol, emulsifier and water;
   (2) granules, wherein the components consist of 4-bromo-2-(4-chlorophenyl)-1-(2-chloro-5-thiazolylmethyl)-5-trifluoromethylpyrrole-3-carbonitrile, sodium dodecylbenzene sulfonate, epoxy resin, pigment red and clay;
   (3) wettable powders, wherein the components consist of 4-bromo-2-(4-chlorophenyl)-1-(2-chloro-5-thiazolylmethyl)-5-trifluoromethylpyrrole-3-carbonitrile, lignin carboxylate, sodium dodecylbenzenesulfonate and kaolin;
   (4) water-dispersible granules, wherein the components consist of 4-bromo-2-(4-chlorophenyl)-1-(2-chloro-5-thiazolylmethyl)-5-trifluoromethylpyrrole-3-carbonitrile, naphthalene sulfonate polycondensate, sodium butylnaphthalene sulfonate, urea, kaolin, water and fructose (binder);

(5) microemulsions, wherein the components consist of 4-bromo-2-(4-chlorophenyl)-1-(2-chloro-5-thiazolylmethyl)-5-trifluoromethylpyrrole-3-carbonitrile, calcium dodecylbenzene sulfonate, styrene phenol polyoxyethylene ether, water and deionized water;

(6) aqueous emulsions, wherein the components consist of 4-bromo-2-(4-chlorophenyl)-1-(2-chloro-5-thiazolylmethyl)-5-trifluoromethylpyrrole-3-carbonitrile, xylene, alkylphenylpolyglycol ether, polyoxyethylene sorbitan ester, polyoxyethylene fatty acid ester, polyvinyl alcohol, isobutyl ester, propylene glycol and deionized water;

(7) emulsifiable concentrates, wherein the components consist of 4-bromo-2-(4-chlorophenyl)-1-(2-chloro-5-thiazolylmethyl)-5-trifluoromethylpyrrole-3-carbonitrile, xylene, sodium dodecylbenzenesulfonate and styrylphenol formaldehyde resin polyoxyethylene.

3. The agricultural insecticide dosage forms prepared using the arylpyrrolecarbonitrile compound as claimed in claim 2, characterized in that preparation of suspensions includes the following steps: a) pre-dispersing 4-bromo-2-(4-chlorophenyl)-1-(2-chloro-5-thiazolylmethyl)-5-trifluoromethylpyrrole-3-carbonitrile, naphthalene sulfonate polycondensate, sodium dodecylbenzene sulfonate, xanthan gum, glycerin and water with a high shear mixing emulsifier to form a slurry; b) pouring the slurry into a sand mill; c) introducing cooling water into the sand mill; d) turning on the sand mill; e) sampling at the discharge port; f) monitoring the particle size with a particle size distribution meter; g) once the median particle size, $D_{50}$, reaches 2-3 microns, a suspension is obtained which contains 25 wt. % of 4-bromo-2-(4-chlorophenyl)-1-(2-chloro-5-thiazolylmethyl)-5-trifluoromethylpyrrole-3-carbonitrile as active ingredient.

4. The agricultural insecticide dosage forms prepared using the arylpyrrolecarbonitrile compound as claimed in claim 2, characterized in that preparation of granules includes the following steps: a) mixing and pulverizing 4-bromo-2-(4-chlorophenyl)-1-(2-chloro-5-thiazolylmethyl)-5-trifluoromethylpyrrole-3-carbonitrile, sodium dodecylbenzene sulfonate, epoxy resin, pigment red and clay; b) granulating the mixture using a disc granulator; c) forming the granules and drying using hot air; d) cooling and sieving the granules by passing the granules through 3 mm and 5 mm sieves; and e) wherein particles passing through the 5 mm sieve and remaining on the 3 mm sieve are the desired granules containing 2 wt. % of 4-bromo-2-(4-chlorophenyl)-1-(2-chloro-5-thiazolylmethyl)-5-trifluoromethylpyrrole-3-carbonitrile as active ingredient.

5. The agricultural insecticide dosage forms prepared using the arylpyrrolecarbonitrile compound as claimed in claim 2, characterized in that preparation of wettable powders includes the following steps: a) mixing and pulverizing 4-bromo-2-(4-chlorophenyl)-1-(2-chloro-5-thiazolylmethyl)-5-trifluoromethylpyrrole-3-carbonitrile, lignin carboxylate, sodium dodecylbenzene sulfonate and kaolin; b) further pulverizing using an ultrafine pulverizer; c) passing the pulverized particle through a 325 mesh sieve to obtain the desired wettable powder containing 10 wt. % of 4-bromo-2-(4-chlorophenyl)-1-(2-chloro-5-thiazolylmethyl)-5-trifluoromethylpyrrole-3-carbonitrile as active ingredient.

6. The agricultural insecticide dosage forms prepared using the arylpyrrolecarbonitrile compound as claimed in claim 2, characterized in that preparation of water-dispersible granules includes the following steps: a) forming a ultrafine wettable powder comprising 4-bromo-2-(4-chlorophenyl)-1-(2-chloro-5-thiazolylmethyl)-5-trifluoromethylpyrrole-3-carbonitrile, naphthalene sulfonate polycondensate, sodium butyl naphthalene sulfonate, urea and kaolin; b) introducing the wettable powder from step a), water and fructose as a binder simultaneously into a kneader; c) kneading the mixture to prepare a plastic material; d) pouring the plastic material into an extrusion granulator for granulation with 3 mm pore size of the sieve; and e) drying and sieving the material to obtain a water-dispersible granule product containing 10 wt. % of 4-bromo-2-(4-chlorophenyl)-1-(2-chloro-5-thiazolylmethyl)-5-trifluoromethylpyrrole-3-carbonitrile as active ingredient.

7. The agricultural insecticide dosage forms prepared using the arylpyrrolecarbonitrile compound as claimed in claim 2, characterized in that preparation of microemulsions includes the following steps: a) mixing thoroughly 4-bromo-2-(4-chlorophenyl)-1-(2-chloro-5-thiazolylmethyl)-5-trifluoromethylpyrrole-3-carbonitrile, calcium dodecylbenzene sulfonate, styrene phenol polyoxyethylene ether and water into a uniform oil phase; b) adding deionized water slowly under stirring; c) heating the reaction under stirring; d) cooling to room temperature; and e) filtering to obtain a microemulsion product containing 20 wt. % of 4-bromo-2-(4-chlorophenyl)-1-(2-chloro-5-thiazolylmethyl)-5-trifluoromethylpyrrole-3-carbonitrile as active ingredient.

8. The agricultural insecticide dosage forms prepared using the arylpyrrolecarbonitrile compound as claimed in claim 2, characterized in that preparation of aqueous emulsions includes the following steps: a) adding 4-bromo-2-(4-chlorophenyl)-1-(2-chloro-5-thiazolylmethyl)-5-trifluoromethylpyrrole-3-carbonitrile, xylene, alkylphenylpolyglycol ether, polyoxyethylene sorbitan ester, polyoxyethylene fatty acid ester, polyvinyl alcohol, isobutyl ester, propylene glycol and deionized water to a formulating kettle for mixing; b) emulsifying using a high shearing machine; and c) mixing the material under the condition of 2500 rpm for 1 hour to obtain a homogeneous aqueous emulsion product containing 10 wt. % of 4-bromo-2-(4-chlorophenyl)-1-(2-chloro-5-thiazolylmethyl)-5-trifluoromethylpyrrole-3-carbonitrile as active ingredient.

9. The agricultural insecticide dosage forms prepared using the arylpyrrolecarbonitrile compound as claimed in claim 2, characterized in that preparation of emulsifiable concentrates includes the following steps: a) adding 4-bromo-2-(4-chlorophenyl)-1-(2-chloro-5-thiazolylmethyl)-5-trifluoromethylpyrrole-3-carbonitrile, xylene, sodium dodecylbenzenesulfonate and styrylphenol formaldehyde resin polyoxyethylene into a reaction vessel; b) mixing the components; and c) allowing the mixture to stand to obtain an emulsifiable concentrate containing 10 wt. % of 4-bromo-2-(4-chlorophenyl)-1-(2-chloro-5-thiazolylmethyl)-5-trifluoromethylpyrrole-3-carbonitrile as active ingredient.

10. A method for preparing an insecticidal arylpyrrolecarbonitrile compound, comprising the following preparation steps:

(1) 2-p-chlorophenyl-4-bromo-5-trifluoromethyl-3-cyanopyrrole, 2-chloro-5-chloromethylthiazole and potassium carbonate are provided as reaction starting materials in a ratio of the amount of substance of 1:1:1.2, and starting materials are put into a three-necked bottle together with DMF;

(2) the materials are reacted at 60 to 100° C. for 1 to 4 hours;

(3) the reaction is stopped after the completion of the reaction of the starting materials is detected, the materials are cooled to room temperature and filtered by suction to give 4-bromo-2-(4-chlorophenyl)-1-(2-chloro-5-thiazolylmethyl)-5-trifluoromethylpyrrole-3-carbonitrile as a white solid.

11. The method for preparing the insecticidal arylpyrrole-carbonitrile compound as claimed in claim 10, characterized in that, in step (1), 35-105 g of 2-p-chlorophenyl-4-bromo-5-trifluoromethyl-3-cyanopyrrole, 17.8-51.4 g of 2-chloro-5-chloromethylthiazole, 17.85-53.55 g of potassium carbonate and 250-750 ml of DMF are added into a three-necked bottle.

12. The method for preparing the insecticidal arylpyrrole-carbonitrile compound as claimed in claim 11, characterized in that, in step (1), 69.9 g of 2-p-chlorophenyl-4-bromo-5-trifluoromethyl-3-cyanopyrrole, 33.6 g of 2-chloro-5-chloromethylthiazole, 33.7 g of potassium carbonate and 500 ml of DMF are added into a three-necked bottle.

13. A method for controlling pests comprising applying the agricultural pesticide dosage forms as claimed in claim 2, to crops and/or pests in a field.

* * * * *